United States Patent [19]

Sogi et al.

[11] 4,210,724
[45] Jul. 1, 1980

[54] APPARATUS FOR LIQUID DISPOSAL AND DISTRIBUTION IN AUTOMATIC CULTURE SYSTEM

[75] Inventors: Shinroku Sogi; Makoto Yoshinaga, both of Hachioji; Toshio Shinohara, Chofu; Takayuki Aihara; Ikuo Tawara, both of Hachioji, all of Japan

[73] Assignee: Olympus Optical Company Ltd., Tokyo, Japan

[21] Appl. No.: 888,036

[22] Filed: Mar. 20, 1978

[30] Foreign Application Priority Data

| Mar. 28, 1977 | [JP] | Japan | 52-33364 |
| Mar. 29, 1977 | [JP] | Japan | 52-38106[U] |
| Apr. 2, 1977 | [JP] | Japan | 52-40253[U] |
| Apr. 4, 1977 | [JP] | Japan | 52-40893[U] |

[51] Int. Cl.² .......................................... C12M 1/26
[52] U.S. Cl. ................................ 435/292; 435/287; 141/130; 141/281; 422/64
[58] Field of Search ................ 195/127; 141/130, 281; 422/64; 366/130, 208; 73/425.4 P; 435/292, 287, 316

[56] References Cited

U.S. PATENT DOCUMENTS

| 3,437,447 | 4/1969 | Harmon | 195/127 X |
| 3,449,959 | 6/1969 | Grimshaw | 73/423 |
| 3,617,222 | 11/1971 | Matte | 422/64 X |
| 3,623,844 | 11/1971 | Anthon | 422/64 |
| 3,735,902 | 5/1973 | Zindler | 222/363 |
| 3,772,154 | 11/1973 | Isenberg et al. | 195/127 X |
| 3,796,239 | 3/1974 | Zindler | 141/83 |
| 3,859,051 | 1/1975 | Natelson | 422/64 |

*Primary Examiner*—Raymond N. Jones
*Assistant Examiner*—Robert J. Warden
*Attorney, Agent, or Firm*—Ostrolenk, Faber, Gerb & Soffen

[57] ABSTRACT

An apparatus for liquid disposal and distribution in automatic culture system comprises a first turntable carrying a plurality of culture vessels disposed in an array on a common circle thereon, and a second turntable carrying a plurality of centrifuge tubes disposed in an array on a common circle thereof. The apparatus comprises a pipette holding arm which is disposed so that its free end is angularly movable between one of the culture vessels and one of the centrifuge tubes. The free end of the arm has attached thereto a tapered cylinder which detachably receives a pipette. A fixed displacement pump is connected with the cylinder, which is movable along the path of rotation, along which are disposed a pipette holder, a pipette remover and a liquid disposal pot. The apparatus also comprises a rotary and elevating mechanism associated with the arm. In this manner, the apparatus is capable of transferring a specimen being cultured from a culture vessel to a centrifuge tube, distributing grown cells from the tube into culture vessels and disposing unnecessary liquid. In addition, the apparatus is capable of agitating a culturing solution within the culture vessel to render the cells into suspension.

14 Claims, 13 Drawing Figures

4,210,724

APPARATUS FOR LIQUID DISPOSAL AND DISTRIBUTION IN AUTOMATIC CULTURE SYSTEM

BACKGROUND OF THE INVENTION

The invention relates to an apparatus for liquid disposal and distribution for use in an automatic culture system which performs an automatic culturing of biological tissues and cells, and more particularly to such apparatus for transferring or distributing cells being cultured from a culture vessel into a centrifuge tube or vice versa and for disposing unnecessary liquid from the culturing vessel.

The technique of culturing biological tissues and cells represents an essential and fundamental experimental process in the study of cells in various fields including the medical, biological, pharmaceutical and agricultural fields. However, the culture of biological tissues and cells over successive generations involves a technical difficulty, which prevents a stable strain being cultured from being obtained in practice. Thus, there has been a need to establish a procedure for culturing biological tissues and cells which makes it possible to obtain a stabilized strain. Recently, a culture technique in a gaseous environment maintained within an incubator has been developed, and has enabled the culturing over successive generations of cells of a particular variety such as those of liver, neuron, pituitary gland, which have been heretofore considered difficult to be cultured.

The culture over successive generations of the kind described will be briefly summarized below. A given number of cells which are to be cultured over successive generations are diluted in a culture solution in the form of a suspension, which is then injected into a culture vessel such as petri dish. The vessel is placed still in an incubator for culturing of the cells under a given atmosphere. After a given period of time, the vessel is removed from the incubator and the growth of cells examined under a microscope. When it is determined that the intended growth of cells has extended to the full extent of the vessel, they are transferred to a strain-free clean bench, and the culture solution in the vessel is withdrawn with a pipette and disposed. Subsequently, a buffer solution is injected into the vessel to clean the remaining cells, and then withdrawn for disposal with a pipette. To render the grown cells which attach to the bottom of the vessel almost freely releasable therefrom, an enzyme solution such as tripsin is injected into the vessel and the latter left intact for a given period. After such period, the enzyme solution is withdrawn from the vessel with a pipette and disposed, and a culture solution is again injected into the vessel. The culture solution is repeatedly withdrawn and discharged through a pipette to cause an oscillation and agitation which enables the grown cells to be completely released from the bottom of the vessel into a suspension in the culture solution. The cells in suspension are transferred into a centrifuge tube with a pipette, and placed in a centrifuge to separate the cells from the solution. Thereupon, the cells remain attached to the bottom of the tube, while the culture solution will be a supernatant solution, which is disposed by tilting the tube. A culture solution is again injected into the centrifuge tube and is agitated by utilizing the withdrawal and discharge operation with a pipette in order to separate the cells from each other so that they are uniformly suspended in the culture solution within the centrifuge tube. Finally, the solution is distributed into a pair of culture vessels in an equal amount to complete one culture operation.

It will be seen that with the culture technique described, it is necessary to remove the culture vessel from the incubator and place it in the outer atmosphere in order to examine the growth of the tissues or cells under the microscope. This causes a sudden change in the culturing condition since the cells or tissues are placed out of the given environment maintained within the incubator including a given gas atmosphere, temperature and humidity. This causes a delicate influence upon the tissues or cells being cultured and also involves an unavoidable contamination by miscellaneous strains present in the atmosphere.

In addition, the various operations required for culturing over successive generations which should take place on the basis of the observation under the microscope, depend on a manual operation by an operator on the clean bench. This means that any slight difference in the various operations which occur from operator to operator may have a direct influence upon the culturing result of the tissues or cells since the experience and skill of culturing technique varies from operator to operator. Thus, it is difficult to provide a standard procedure for the culturing technique which makes it impossible to obtain cultured tissues or cells of uniform quality. As a consequence of this, different groups of researchers, conducting a common study on the same theme, may reach different conclusions, depending on the quality of the tissues being cultured. In extreme cases, the conclusions may be opposite to each other. Thus it will be seen that the reliability cannot be expected when the tissues or cells are cultured with the conventional technique.

It is generally accepted that the training of a skilled operator requires at least two years. As a result, there has been a continued shortage of skilled operators. It has therefore become necessary for the researchers to perform the culturing operation themselves rather than devotedly directing their efforts to their study.

In view of these considerations, the present invention is directed towards an automatic culture system capable of performing the described culturing operations automatically in order to eliminate the contamination which may occur as a result of the exposure of the tissues or cells being cultured to the atmosphere and to eliminate the influence of manual operations upon the cultured results, thereby permitting a standard and uniform procedure to be adopted for conducting the various culturing operations.

As will be appreciated from the foregoing description, this automatic culture apparatus is able to withdraw and dispose from the culture vessel a liquid such as culturing, buffer and enzyme solution, to render grown cells in the culture vessel as a suspension in a fresh culturing solution for distribution into the centrifuge tube. The apparatus is further able to separate the centrifuged cells from each other for suspension in a fresh culturing solution in order to permit their distribution into a pair of fresh culture vessels in an equal amount. In the present apparatus, these operations are performed by a fixed displacement pump of a syringe type which is connected with a pipette for conducting a withdrawal and discharge operation. However, it will be appreciated that when such pipette is used, the admixture of a liquid from a previous step with a fresh solution delivered into the culture vessel or centrifuge tube during the next following step must be avoided since otherwise there occur adverse influences upon the culturing result. Hence, the fresh one must be used for each operation. Furthermore, as mentioned previously, before the grown cells are transferred into the centrifuge tube, the culturing solution within the vessel is repeatedly withdrawn and discharged with a pipette to cause an agitation of the cells so that they are completely released from the bottom of the vessel and rendered as a suspension in the culturing solution. It is desirable that such agitation be achieved with a high efficiency.

SUMMARY OF THE INVENTION

It is a principal object of the invention to provide an apparatus for liquid disposal and distribution in an automatic culture system in which a used pipette is automatically disposed upon completion of an operating step and a fresh pipette is automatically mounted before the next following step is conducted so that liquid disposal and distribution are performed using separate pipettes, thus enabling a liquid disposal and distribution to be achieved in a single apparatus.

It is another object of the invention to provide an apparatus of the kind described which includes a withdrawal and discharge pump connected with the pipette and which is sophisticated in a manner to avoid the problem of contamination, by merely replacing the pipettes between different operations.

It is a further object of the invention to provide a pipette holder which facilitates an automatic loading of a fresh pipette on a pipette receiving position as it is fed one by one from a pipette feeder and which can be automatically removed from such position subsequent to the loading step.

It is still another object of the invention to provide an apparatus for agitating a culturing solution in an automatic culture system which achieves the agitation of the solution to release cells from the bottom of the culture vessel with a high efficiency.

In accordance with the invention, a single apparatus can be used for liquid disposal and distribution, and thus reduces the space requirement and the cost as compared with the provision of separate arrangements for such purposes. The withdrawal and discharge pump used in the present invention has a capacity which is less than the volume of a pipette.

As a consequence, during the disposal step in which unnecessary liquid such as culturing, buffer or enzyme solution is to be disposed from the culture vessel, during the distribution step in which the grown cells are separated into a uniform suspension in a fresh culturing solution for distribution into the centrifuge tube, or during the distribution step in which the centrifuged cells are freed into a fresh culturing solution supplied into the centrifuge tube to provide a uniform suspension which is then distributed into a pair of fresh vessels in an equal amount, the amount of liquid which is introduced into the pipette cannot exceed the volume thereof, thus effectively limiting the extent of contamination by such liquid to the region of the pipette. Thus, a mere replacement of pipettes between different steps is sufficient to positively prevent the mixture of an old and a fresh liquid.

In accordance with the invention, the liquid disposal operation and the distribution operation are performed by an angular movement of a pipette holding arm. This enables a compact arrangement to be obtained even though the pipettes must be replaced between different steps. Optionally, signals from various switches or encoders may be fed to a central control system such as computer, which may be programmed to follow a predetermined operating procedure, thus achieving a perfect automation of the entire operation. The pipette holder is formed with a tapered opening which accurately locates a fresh pipette on a pipette loading position, as it is fed one by one from a pipette feeder, thus facilitating an automatic loading of the pipette in a pipette receiving cylinder.

The invention also provides an apparatus for agitating a culturing solution which comprises means for periodically tilting a pipette in a culturing solution contained in a culture vessel while it is immersed therein, and means for causing the pipette to withdraw and discharge the solution in synchronism with the tilting operation. This greatly improves the agitating efficiency.

DESCRIPTION OF PREFERRED EMBODIMENTS

Figure 1:
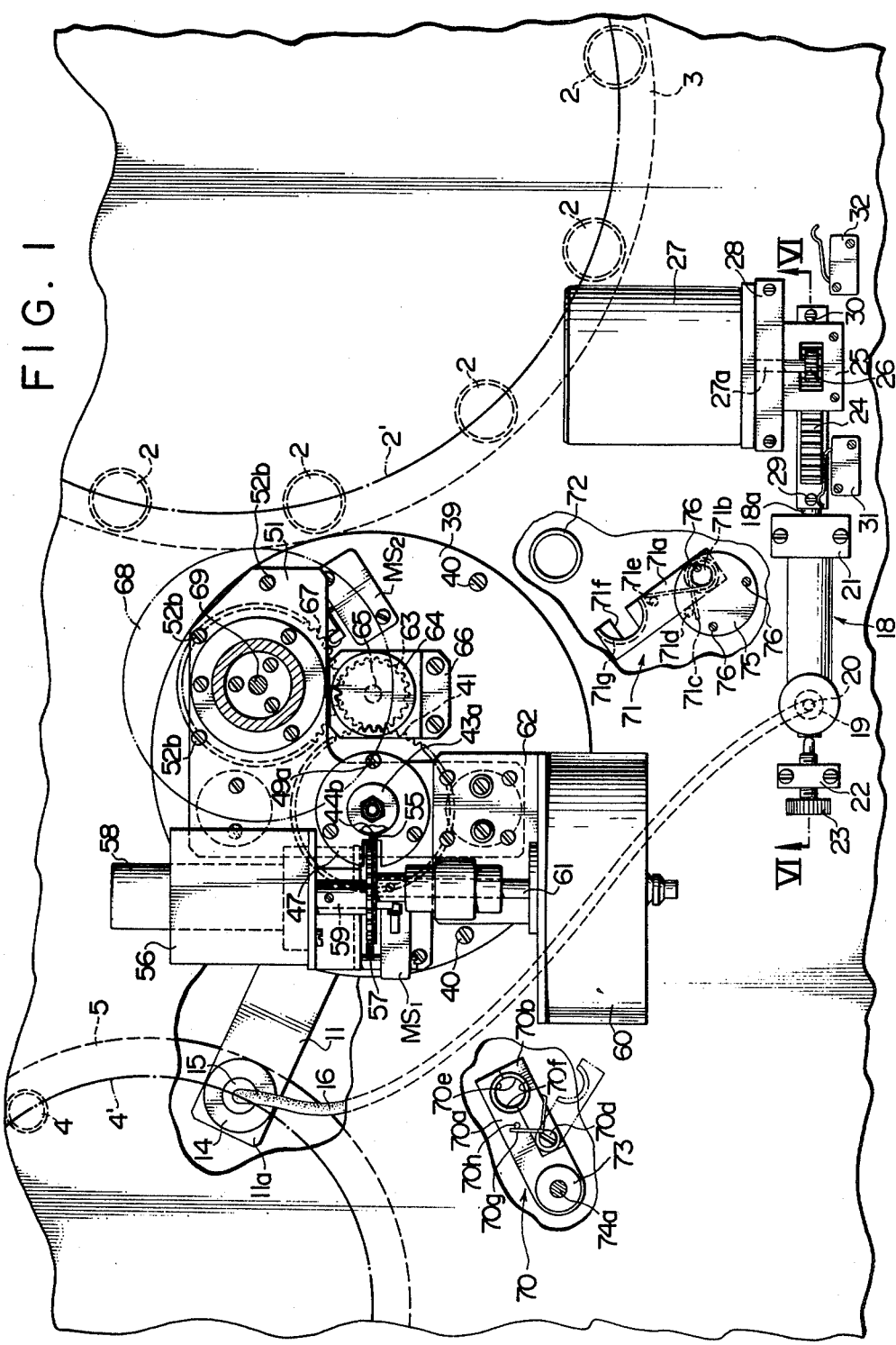
FIG. 1 is a plan view, partly broken away, of the apparatus constructed according to one embodiment of the invention.
Figure 4:
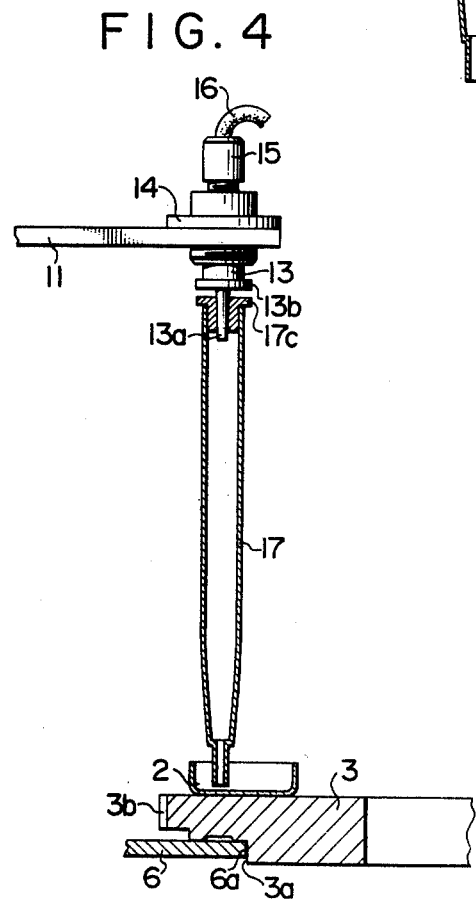
FIG. 4 is a side elevation, partly in section, of a culture vessel on a first turntable and a pipette.
Figure 5:
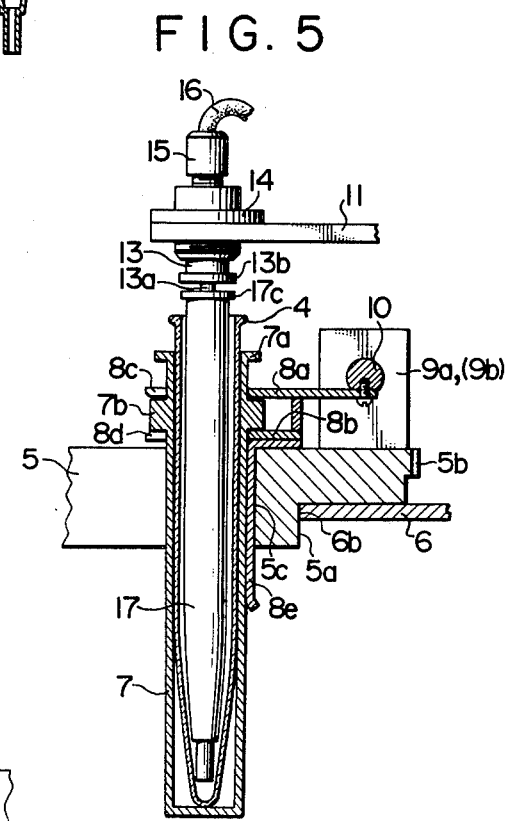
FIG. 5 is a side elevation, partly in section, of a centrifuge tube held on a second turntable and a pipette.

Referring to FIG. 1, there is shown an incubator having a top wall 1 which is stationary. A plurality of culture vessels 2, which are schales in the example shown, are equally spaced about a common circumference of a first turntable 3. A plurality of centrifuge tubes 4 are equally spaced about a common circumference of a second turntable 5. It is to be understood that both the vessels 2 and the tubes 4 are disposed inside the incubator. Both turntables 3 and 5 are rotatably mounted in horizontal position. The centrifuge tube 4 is adapted to be loaded into a centrifuge in order to separate grown cells from a culturing solution which is contained therein. As shown in FIG. 4, the first turntable 3 is rotatably disposed on a stationary mounting plate 6 which is horizontally disposed within the incubator, by engaging a circular edge 3a of a reduced diameter formed around the bottom of its circumference with an opening 6a formed in the plate 6. The turntable 3 is peripherally formed with a gear 3b, which meshes with a drive gear, not shown, so that it is intermittently driven for rotation through a given angular increment corresponding to the angular pitch between the culture vessels 2 when the drive gear is driven by a pulse motor or the like. As shown in FIG. 5, the second turntable 5 is also rotatably disposed on the plate 6, by fitting a circular edge 5a formed around the lower surface of its periphery with another opening 6b formed in the plate 6. The turntable 5 is also peripherally formed with a gear 5b, which meshes with a drive gear, not shown, so that it is intermittently driven for rotation through a given angular increment corresponding to the angular pitch between adjacent centrifuge tubes 4 when the drive gear is driven by a pulse motor or the like.

Referring to FIG. 5, the centrifuge tube 4 is detachably received in a centrifuge tube holder 7 which comprises a cylinder having a bottom, which is in turn detachably mounted on a support mechanism disposed on the turntable 5. The support mechanism comprises a pair of sideplates 9a, 9b fixedly mounted on the turntable 5, a shaft 10 extending horizontally across and rotatably supported by the sideplates, and a pair of upper and lower support plates 8a, 8b having their one end connected together and connected with the shaft 10 and formed with semi-circular recesses 8c, 8d in their free end. The holder 7 is provided with a top opening around which a flange 7a is formed. Intermediate its length, the holder 7 is formed with another flange 7b which is adapted to engage the recesses 8c, 8d to be held sandwiched between the pair of support plates 8a, 8b. When the holder 7 is moved into alignment with a distribution station or a loading station into the centrifuge as the turntable 5 rotates, it rotates counter-clockwise about the shaft 10 by gravity to be held in its upright position as shown. Specifically, a follower plate 8e is secured to the lower support plate 8b and cooperates with a cam edge 5c formed in the turntable 5 to maintain the holder 7 in its upright position whenever it is in alignment with the above stations. However, in other positions, the holder 7 is maintained in a tilted position as a result of the cooperation between the cam edge 5c and the follower plate 8e. The purpose of causing the holder to assume such a tilted position is to prevent the ingress of miscellaneous strains into the centrifuge 4.

Figure 2:
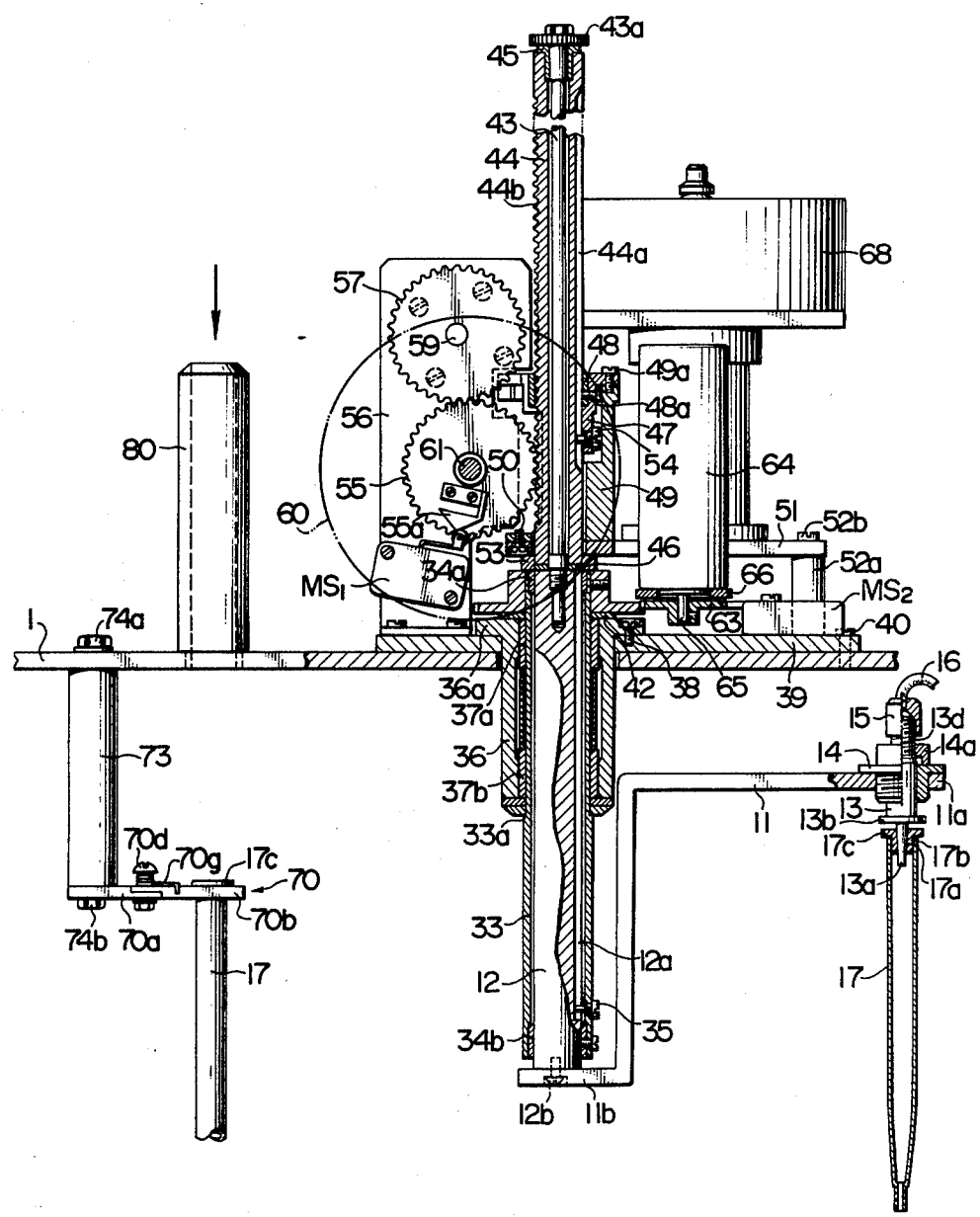
FIG. 2 is a fragmentary longitudinal section of the apparatus shown in FIG. 1.

The apparatus for liquid disposal and distribution of the invention is disposed between the first and second turntables 3, 5 as shown in FIG. 1. In this Figure, it will be noted that the culture vessels 2 are disposed on a common circle 2' of the turntable 3 while the centrifuge tubes 4 are disposed on a common circle 4' of the turntable 5. The apparatus comprises a pipette holding arm 11 having a free end 11a which is angularly movable between a position intersecting with the circle 2' and another position intersecting with the circle 4'. As shown in FIG. 2, the arm 11 is crank-shaped and has its opposite end 11b secured to the lower end face of an elevating shaft 12 by means of a set screw 12b. The shaft 12 extends through the top wall 1 and depends vertically into the incubator, and is adapted to be driven by a rotary and elevating mechanism to be described later.

Figure 3:
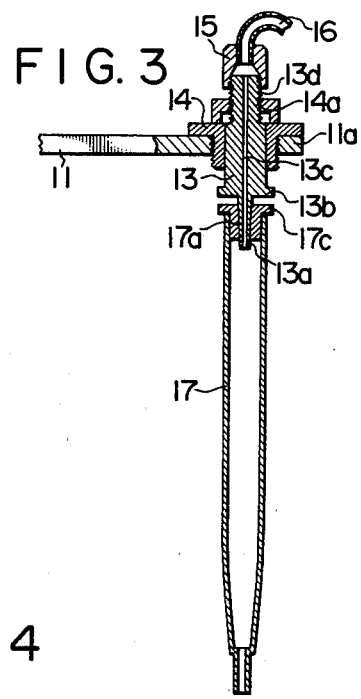
FIG. 3 is a longitudinal section of a pipette and a pipette receiving cylinder.
Figure 6:
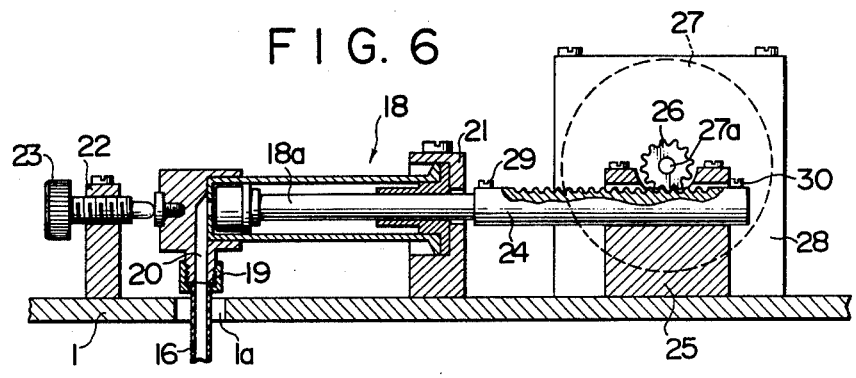
FIG. 6 is a cross section taken along the line VI—VI shown in FIG. 1.

A pipette fitting cylinder 13 is secured in the free end 11a of the arm 11 by means of a mounting nut 14, and hence can be brought into a position directly above the culture vessel 2 or centrifuge tube 4 when the arm 11 moves angularly. Referring to FIGS. 2 and 3, the cylinder 13 is formed with a downwardly depending, tapered projection 13a and is also provided with a flange 13b intermediate its length. In addition, an axial bore 13c is formed in alignment with the axis of the cylinder. The nut 14 threadably engages the free end 11a and receives the cylinder 13, which is provided with a threaded top end 13d for screwed connection with a threaded element 14a which is integral with the nut 14. The tapered projection 13a tightly fits in a central opening 17a formed in a plug 17b which is fixedly connected with the top opening of a pipette 17, thus detachably holding the latter. It will be understood that the central opening 17a is also tapered in a manner corresponding to the tapering of the projection 13a to form a hermetic seal with the projection 13a as the latter is inserted. A coupling 15 is engaged with the top end of the cylinder 13 and receives one end of a tubing 16. As shown in FIG. 1, the tubing 16 connects the cylinder 13 with a fixed displacement pump 18, the other end of the tubing 16 being connected with the withdrawal and discharge port 20 of the pump 18 through a fitting 19. The pump 18 is mounted on the top wall 1 between a pair of mounting members 21, 22, by clamping a mounting screw 23, and has its port 20 connected with the other end of the tubing 16 which extends through an opening 1a formed in the plate 1 (see FIG. 6).

In accordance with the invention, the pump 18 comprises a fixed displacement pump of syringe type having a capacity which is less than the volume of the pipette 17. The pump 18 includes a piston rod 18a which is integrally connected with a rack 24, which is guided by a guide member 25 mounted on the stationary wall 1 and which meshes with a pinion 26. The pinion 26 is fixedly mounted on the output shaft 27a of a reversible motor 27 which is in turn mounted on the stationary wall 1 by using a bracket 28. It will be seen that the rotation of the motor 27 in opposite directions causes an axial movement of the piston rod 18a through the pinion 26 and rack 24 to enable the pump 18 to withdraw or discharge a liquid. The stroke of the piston rod 18a is limited by a pair of screws 29, 30 which are disposed for abutment against the opposite sides of the guide member 25, these screws also serving as actuators for a pair of microswitches 31, 32 (see FIG. 1) which control the motor 27.

FIG. 2 shows the rotary and elevating mechanism associated with the pipette holding arm 11. The elevating shaft 12 is driven in the vertical direction as a result of the meshing engagement between a rack 44b and a gear 55 which is in turn driven by a motor 58 (see FIG. 1). The rotation of the elevating shaft 12 is achieved through a gear 41 which is in turn driven by a motor 64. A pair of encoders 60, 68 are provided for controlling the motors 58, 64.

Specifically, the elevating shaft 12 extends through and is rotatable inside a sleeve 33, and is provided at its upper and lower ends with a pair of bushing 34a, 34b which fit in the sleeve to prevent a lost motion. The shaft 12 is formed with a longitudinal flute 12a, which is engaged by the free end of a pin 35 that is threadably engaged with the bottom end of the sleeve 33 and extends in the radial direction. Thus, the shaft 12 is vertically movable with respect to the sleeve 33, but rotate integrally with the sleeve 33.

The sleeve 33 is rotatably received in a bearing sleeve 36 which extends through the stationary wall 1 and a fixed disc 39. The disc 39 is secured to the stationary wall 1 by screws 40, and the bearing sleeve 36 is mounted on the disc 39 by fixedly connecting its top flange 36a with a set screw 38. A pair of bushings 37a, 37b are disposed inside the bearing sleeve 36 at its upper and lower ends, and rotatably receives the sleeve 33. The disengagement of the sleeve 33 from the bearing sleeve 36 is prevented by a shoulder 33a on the sleeve 33 which engages the lower end of the sleeve 36, and a gear 41 fixedly mounted on an upper portion of the sleeve 33 which projects above the sleeve 36. A spacer 42 is interposed between the upper end face of the bearing sleeve 36 and the gear 41 to reduce the friction therebetween.

An extension shaft 43 of a reduced diameter is treadably engaged with the upper end face of the elevating shaft 12 and is in axial alignment with the latter. The extension shaft 43 rotatably extends through another sleeve 44 which is provided for the purpose of elevating the shaft 12. The sleeve 44 has the same diameter as the shaft 12, and an enlarged head 43a is secured to the upper end of the shaft 43 which projects above the sleeve 44, with a flanged bearing 45 interposed between the head and the upper end of the shaft 43 to prevent the disengagement of the shaft 43 from the sleeve 44. A spacer 46 is interposed between the lower end of the sleeve 44 and the elevating shaft 12 in order to reduce the friction therebetween.

Intermediate its length, the elevating sleeve 44 passes through a guide ring 48 so as to be capable of smoothly moving in the vertical direction. The ring 48 is secured to a flanged mounting member 47 by means of set screw 48a, and the mounting member 47 is disposed inside a stationary cylinder 49 and secured to the top end thereof by set screw 49a. The lower end of the stationary cylinder 49 is secured, by set screw 50, to a mounting plate 51, which is in turn fixedly connected with the fixed disc 39 by utilizing a stub shaft 52a and set screw 52b.

As shown in FIG. 1, the mounting plate 51 has an inverted L-shaped configuration in top view, and the end of its horizontal portion, as viewed in FIG. 1, is secured to the disc 39 in the upper, right-hand region thereof. The plate 51 has a free end portion, through which the elevating sleeve 44 and the extension shaft 43 extend and which is supported by an annulus 53 placed on the top end face of the sleeve 33.

A locking pin 54 threadably engages the mounting member 47 and extends therethrough into a longitudinal flute 44a formed in the sleeve 44, thus preventing a rotation of the sleeve 44. The sleeve 44 is formed with the axially extending rack 44b which meshes with the drive gear 55, which in turn meshes with output gear 57 fixedly mounted on the output shaft 59 of the motor 58 (see FIG. 1). The motor 58 is mounted on a bracket 56 which is fixedly mounted on the disc 39, and the drive gear 55 is fixedly mounted on the input shaft 61 of an encoder 60. The encoder 60 is mounted on a bracket 62 (see FIG. 1) which is secured to the disc 39. The gear 55 carries, on its lateral side, an actuator 55a which operates a microswitch MS1, the microswitch being operated by the actuator 55a as the gear 55 rotates. The switching signal is supplied to the encoder 60. The vertical displacement of the pipette holding arm 11 is controlled by the encoder 60 which detects an angle through which the gear 55 rotates and which deenergizes the motor 58 when the pipette 17 reaches given level or elevation.

As mentioned previously, the elevating shaft 12 is driven for rotation by the gear 41, which meshes with an output gear 63 fixedly mounted on the output shaft 65 of the motor 64, which is in turn mounted on a bracket 66 secured to the disc 39. The gear 63 meshes with another gear 67 fixedly mounted on the input shaft 69 of an encoder 68, as shown in FIG. 1, the latter being mounted on the mounting plate 51. The encoder 68 operates to detect an angular displacement of the pipette holding arm 11 to deenergize the motor 64 when the pipette 17 has been rotated through a given angle. The encoder 68 receives an input signal from the microswitch MS2 which is operated by an actuator, not shown, attached to the gear 67.

As shown in FIG. 1, a pipette holder 70, a pipette remover 71 and a liquid disposal pot 72 are disposed on the path of rotation of the pipette receiving cylinder 13 which is secured to the arm 11. The location of these components represents a pipette fitting position, pipette removal position and liquid disposal position, respectively, which are disposed on said path along which the cylinder 13 rotates during the rotation of the holding arm 11 through nearly one-half revolution, namely, while it moves counter-clockwise from the position of one of the centrifuge tubes 4 to the position of one of the culture vessels 2. It will be appreciated that the pipette fitting position is located toward the second turntable 5 while the liquid disposal position is located toward the first turntable 3. The pipette removal position is located between such two positions.

Referring to FIGS. 1, 2, 7 and 9, the pipette holder 70 comprises a guide sleeve 80 (see FIG. 2), which directs a pipette 17 for free wheel toward a given position as it is supplied one by one from a pipette feeder, not shown. The holder 70 also comprises a pipette loading plate 70a which is disposed below the guide sleeve 80. A semi-circular notch is formed in a free end thereof which is located in vertical alignment with guide sleeve 80. Set screw 74b secures one end of the loading plate 70a to the lower end face of a stanchion 73 which is secured to the stationary plate 1 by set screw 74a, and the plate is held in its horizontal position. A movable piece 70b has a notch of a complementary shape to that of the notch formed in the loading plate 70a, and is pivotally mounted on a stud 70d which is fixedly mounted on the plate 70a. A torsion spring 70g is disposed on the stud to urge the movable piece 70b into mating relationship with the adjacent edge of the loading plate 70a so that a circular slot 70e having a tapered edge 70f is defined by the notches of the loading plate and the movable piece for receiving the flange of the pipette 17. The spring 70g has its one end bearing against a pin 70h fixedly mounted on the plate 70a and its other engaged with a lateral edge of the movable piece 70b, thus urging the latter to rotate counter-clockwise about the stud 70d. It is to be noted that the movable piece 70b is sized and disposed so that its upper surface is level with that of the plate 70a. The circular slot 70e is in vertical alignment with the guide sleeve 80, and has a dimension to receive the pipette 17 by a fitting engagement therewith. When the pipette 17 is received in the circular slot, its flange 17c engages the tapered edge 70f, thereby centering the pipette 17 on the path of movement of the pipette fitting cylinder 13 (see FIG. 7).

Figure 8:
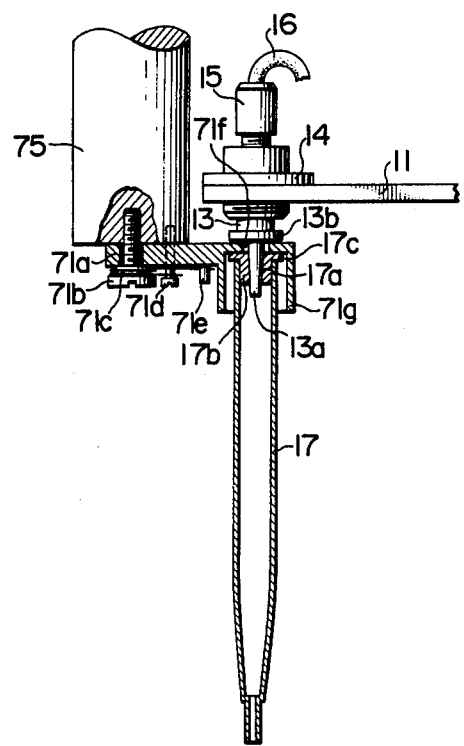
FIG. 8 is a side elevation, partly in section, of a pipette remover which is shown in a broken region of FIG. 1, with the cylinder engaged with the pipette.
Figure 9:
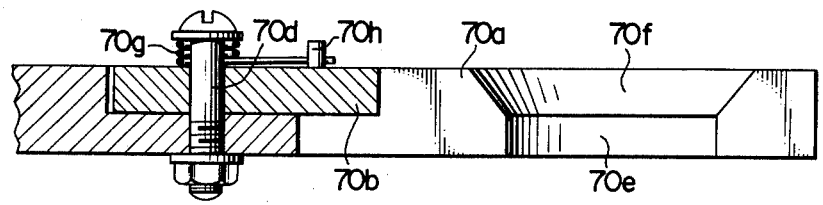
FIG. 9 is a fragmentary enlarged view of the pipette holder shown in FIG. 7.
Figure 11:
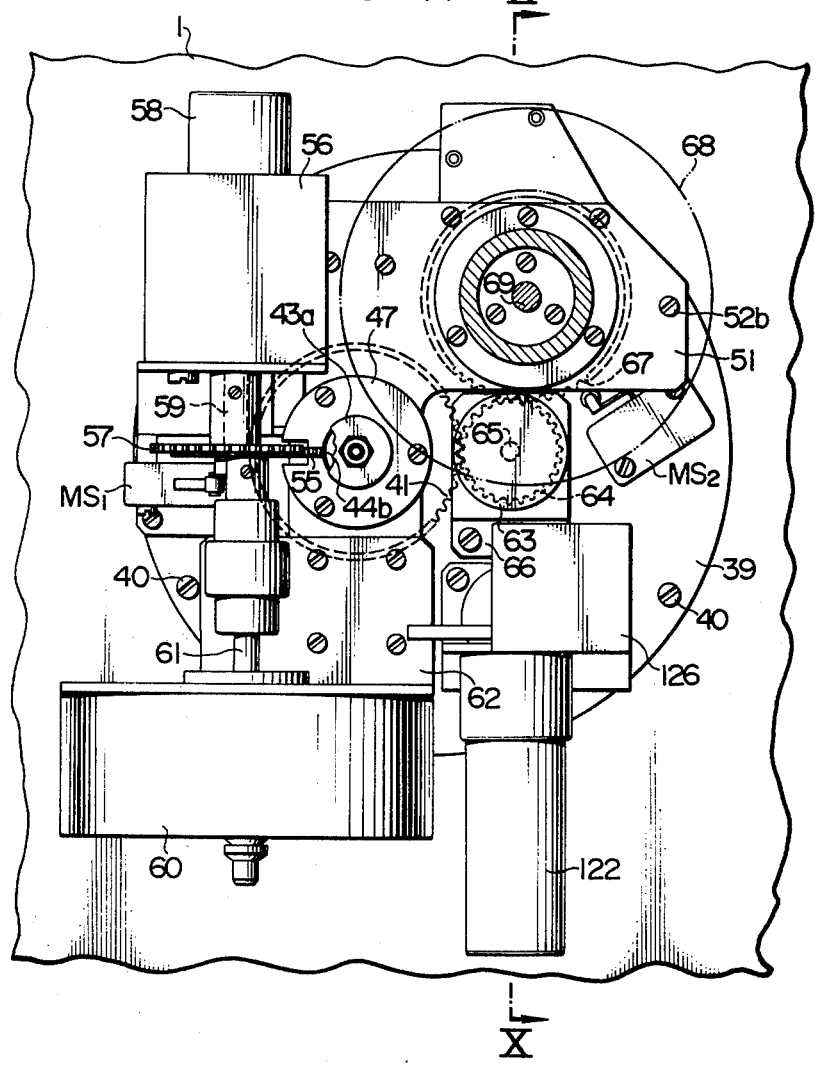
FIG. 11 is a plan view of the agitation apparatus shown in FIG. 10.

Referring to FIGS. 1 and 8, the pipette remover 71 comprises a stationary shaft 75 and a removal arm 71a which is pivotally mounted on the lower end of the shaft 75 by means of a set screw 71b. The shaft 75 has its upper end secured to the underside of the stationary plate 1 by set screw 6 and depends downwardly therefrom. A torsion spring 71c is disposed on the screw 71b and has its one end engaged with a depending pin 71d from the shaft 75 and its other end engaged with a depending pin 71e from the removal arm 71a for urging the arm 71a into abutment against the pin 71d. When so located, the free end of the arm 71a is located over the path of rotation of the cylinder 13. A semi-circular slot 71f is formed in the free end of the arm 71a so as to engage the underside of the flange 13b of the cylinder 13. A semi-cylindrical cover 71g surrounds the slot 71f and downwardly depends from the arm 71a. The slot 71f can be engaged with the tapered projection 13a of the cylinder 13 which is exposed between the flange 13b and the top end of the pipette, and the cylinder 13 may be moved upward to remove the pipette 17 from the projection 13a.

Referring to FIG. 1, the liquid disposal pot 72 is disposed on the path along which the pipette 17 is moved as the arm 11 rotates, and unnecessary culture solution can be withdrawn from the culture vessel 2 into the pipette 17 and discharged into the pot 72 by means of the pump 18.

Figure 7:
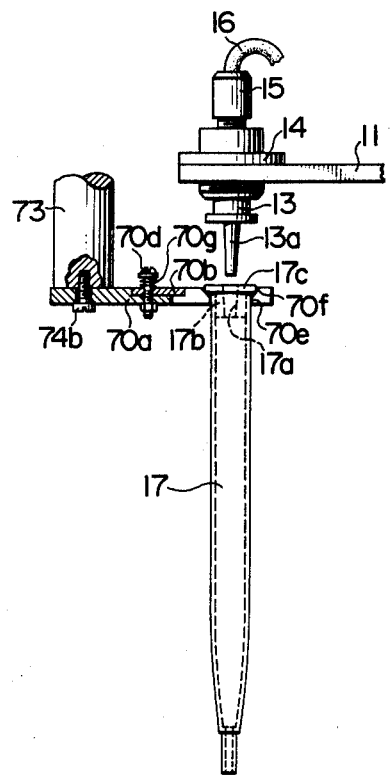
FIG. 7 is a side elevation, partly in section, of a pipette holder which is shown in a broken region of FIG. 1, with the cylinder being brought into alignment with the pipette.

It is to be understood that a sterilized, fresh pipette 17 is maintained in a centered, upright position within the circular slot 70e. When fitting a pipette 17 into the cylinder 13, the motor 58 is set in motion in either direction, thus vertically moving the sleeve 44 through the gears 57, 55 and rack 44b. The vertical motion is transmitted through the extension shaft 43 to the elevating shaft 12, which moves vertically together with the arm 11 as guided by the pin 35 and the longitudinal flute 12a. This vertical movement is detected by the encoder 60, which deenergizes the motor 58 when the cylinder 13 carried by the arm 11 assumes such a relative position to the pipette holder 70 as shown in FIG. 7, thus maintaining the cylinder 13 at such level. Subsequently or simultaneously, the motor 64 is set in motion in either direction, driving the gear 63 for rotation. The rotation is transmitted through the gear 41 to the sleeve 33, and thence through gear 67 to the encoder 68. The rotation of the sleeve 33 is transmitted through the pin 35 and flute 12a to the elevating shaft 12, which therefore causes the arm 11 to rotate about its axis. This rotation is detected by the encoder 68, which deenergizes the motor 64 when the sleeve 33 reaches a position shown in FIG. 7 in which it is located directly above the circular slot 70e and hence the tapered opening 17a in the pipette 17. Then, the motor 58 is again set in motion to cause the arm 11 to move down to insert the projection 13a into the tapered opening 17a until the both members are fitted together to achieve a hermetic seal.

Subsequently when it is desired to dispose the liquid from the pipette 17, the motor 64 is set in motion to rotate the arm 11 in the counter-clockwise direction by the transmission as mentioned above. The pipette then moves the movable piece 70b angularly from the closed position shown in solid line to the open position shown in phantom line in FIG. 1, and after being disengaged from the slot 70e, moves with the arm 11 while remaining in fitting engagement with the cylinder 13. The movable piece 70b is then automatically closed by the spring 70g, and thus is capable of receiving a fresh pipette in the slot 70e when it is supplied. During such movement of the pipette 17, it bears against the pipette remover 71, which however does not interfere with the movement of the pipette since the removal arm 71a angularly moves about the set screw 71b against the resilience of the spring 71c as it is driven by the pipette 17. The described rotation of the arm 11 is interrupted by deenergizing the motor 64 in response to a signal from the encoder 68 when the pipette 17 reaches a position above a culture vessel 2 located at an indexed position. Then, the motor 58 is set in motion to lower the pipette 17 into the vessel 2 as shown in FIG. 4, and is deenergized in response to a signal from the encoder 60 which detects that the pipette 17 has moved down to a given level relative to the vessel 2, thus maintaining the pipette 17 at such level.

Subsequently, the motor 27 associated with the pump 18 is energized to activate the pump 18 for its withdrawal stroke, by driving the piston rod 18a through the pinion 26 and its meshing rack 24. The withdrawal is interrupted when the screw 29 abuts against the guide member 25, the screw 30 then operating the microswitch 32 to deenergize the motor 27. The motor 64 is then energized to bring the pipette 17 to a position over the pot 72 under the control of the encoder 68. When such position is reached, the motor 27 is driven in the opposite direction to drive the piston rod 18a through the reverse stroke, causing the pump 18 to perform a discharge operation. The discharge operation is interrupted when the screw 30 abuts against the guide member 25, the screw 29 then operating the microswitch 31 to deenergize the motor 27. The discharge action drives unnecessary culturing solution contained in the pipette 17 into the pot 72 for disposal.

The pipette 17 from which the liquid has been disposed is then disposed by the pipette remover 71. At this end, the motors 58 and 64 are energized under the control of the encoders 60 and 68 to bring the pipette 17 to a position shown in FIG. 8 where it is located below the removal arm 71a. The projection 13a now extends into the fitting slot 71f, and under this condition, the motor 58 is energized to raise the arm 11 through a given stroke or until the projection 13a is located above the arm 71a under the control of the encoder 60, thus removing the pipette 17 from the projection 13a for disposal.

Subsequent to the removal of the pipette 17, the cylinder 13 is returned to the position shown in FIG. 7 where it is located directly above the tapered opening 17a of a fresh, sterilized pipette 17 which is maintained by the pipette holder 70, such returning movement being effected with the energization of the motors 58, 64 and under the control of the encoders 60, 68. The projection 13a can then be inserted into fitting engagement with the tapered opening 17a so as to form a hermetic seal with the fresh pipette. This completes one cycle of operation.

By repeating the described cycle, a culturing solution, buffer solution or enzyme solution contained in a culture vessel 2 located at an indexed position is subjected to liquid disposal by using a fresh pipette, and can be supplied with a fresh culturing solution while it is maintained at the indexed position. The pipette 17 maintained in hermetic fitting engagement with the projection 13a is lowered into the culture vessel as shown in FIG. 4. When the motor 27 is continuously driven in alternate directions under this condition, the pump 18 repeats the withdrawal and discharge of the liquid contained in the culture vessel through the pipette 17, the pump acting through a body of air present in pneumatic system extending to the opening 13c. As a consequence, the cells which attach to the bottom of the vessel 2 are separated from each other and rendered as a uniform suspension in the culturing solution. The cells in suspension can be withdrawn into the pipette 17 by the suction action of the pump 18, and the pipette can be brought to a position over a centrifuge tube 4 which is located at an indexed position, by energizing the motors 58 and 64 under the control of the encoders 60 and 68. The pump 18 can be activated for discharge operation to inject the cells from the pipette 17 into the centrifuge tube 4, thus completing the distribution of the cells from the culture vessel 2 to the centrifuge tube 4.

The centrifuge tube which is supplied with grown cells from the culture vessel 2 is transferred together with the holder 7 from the turntable 5 to a centrifuge, not shown, with a suitable transfer mechanism, and the cells are centrifuged from the culturing solution by the centrifuge. Subsequently, the centrifuge tube 4 with its associated holder 7 is returned to the turntable 5 where it is held by a suitable support mechanism (see FIG. 5), and the supernatant culturing liquid is disposed from the centrifuge tube 4 by tilting the latter during the intermittent rotation of the turntable 5. A fresh culturing solution is then injected into the centrifuge tube 4, which is then held in standby condition at an indexed position.

A fresh pipette 17 fitted over the cylinder 13 is then brought into the centrifuge tube 4 located at the standby position, as shown in FIG. 5, by energizing the motors 58, 64 under the control of the encoders 60, 68. The motor 27 is then continuously driven in alternate directions to cause the pump 18 to withdraw or discharge the liquid contained in the centrifuge tube into or out of the pipette 17, thus separating the cells which attach to the bottom of the tube 4 from each other to form a uniform suspension in the culturing solution. One-half of the suspension is injected into an empty culture vessel 2 located at an indexed position, by withdrawing it into the pipette 17 by the suction of the pump 18, moving the pipette to a position over the indexed vessel 2 by the energization of the motors 58, 64 under the control of the encoders 60, 68, and discharging the suspension from the pipette into the vessel 2 by the discharge operation of the pump 18. The pipette 17 is then returned to the position shown in FIG. 5, again energizing the motors 58, 64 under the control of the encoders, and the remainder of the suspension in the centrifuge tube 4 is injected under another empty vessel 2 by a similar operation.

Figure 10:
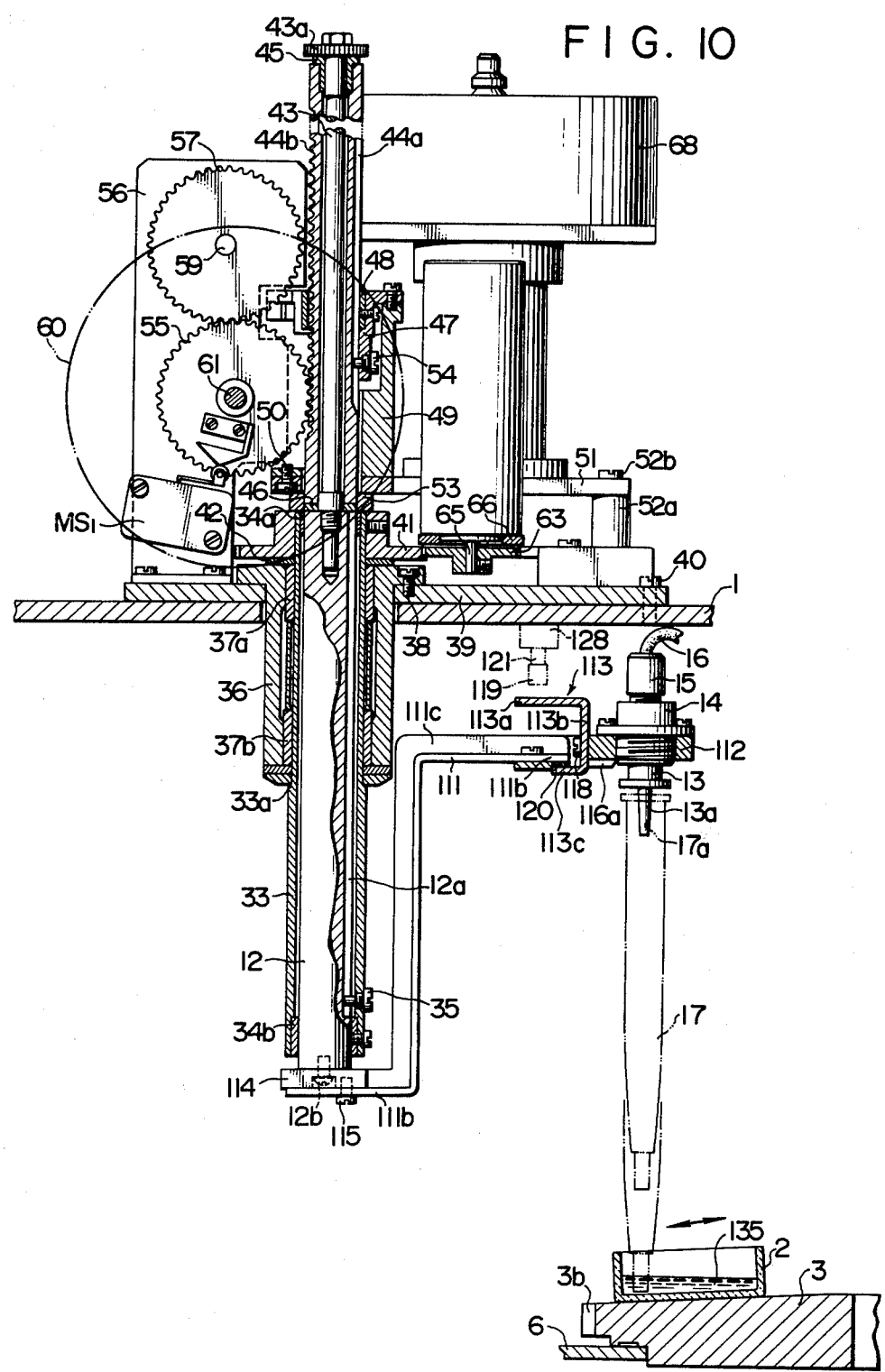
FIG. 10 is a longitudinal section of an agitation apparatus according to the present invention.
Figure 12:
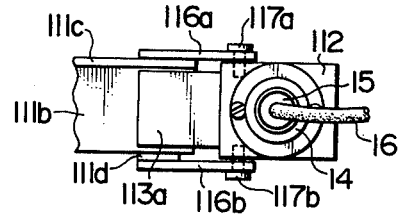
FIG. 12 is a plan view of a support member which supports the cylinder.

In accordance with the invention, there is also provided an apparatus for agitating the culturing solution. In this apparatus, the cylinder 13 is mounted in a tiltable manner so that it can be periodically tilted while maintaining the pipette 17 which is retained thereby immersed in the culturing solution contained in the culture vessel 2. The tilting movement takes place simultaneously with the operation of a fixed displacement pump which repeats the withdrawal and discharge of the solution into and out of the pipette. Referring to FIG. 10, the cylinder 13 is fixedly mounted on a support member 112 which is tiltably mounted on a free end of a pipette holding arm 111. The cylinder 13 is normally maintained in its upright position by a tilting driver 113 which is secured to the support member 112. As before, the pipette holding arm 111 is crank-shaped in configuration and has its one end 111b secured, by set screw 115, to a distance piece 114 which is in turn secured to the lower end face of the elevating shaft 12 by set screw 12b. On one lateral edge, the arm 111 is formed with a sidewall 111c, and an opposite sidewall 111d (see FIG. 12) is formed along the opposite lateral edge of the other end 111b. Referring to FIG. 12, a pair of brackets 116a, 116b have their one end secured to the outside of the sidewalls 111c, 111d and have their other end threadably engaged by a pair of screws 117a, 117b, which are disposed in axial alignment. At its one end, the support member 112 is pivotally mounted on the pair of screws 117a, 117b. As shown in FIG. 10, the tilting driver 113 is channel-shaped in section and is integrally connected with the support member 112, by securing the vertical portion 113b thereof against the inner side of the member 112 by set screw 118. The driver 113 includes a pair of vertically spaced, horizontal limbs 113a, 113c which extend toward the arm 111. The upper horizontal limb 113a is located opposite to a pusher member 119 of a tilting mechanism to be described later. The lower limb 113c bears against a resilient member 120 which is attached to the lower surface of the free end portion 111b of the arm 111, thus defining a normal position for the support member 112 which causes the pipette 17 to assume an upright position. It will be seen that the cylinder 13 is mounted in the support member 112 in the manner mentioned above in connection with FIGS. 2 and 3.

Figure 13:
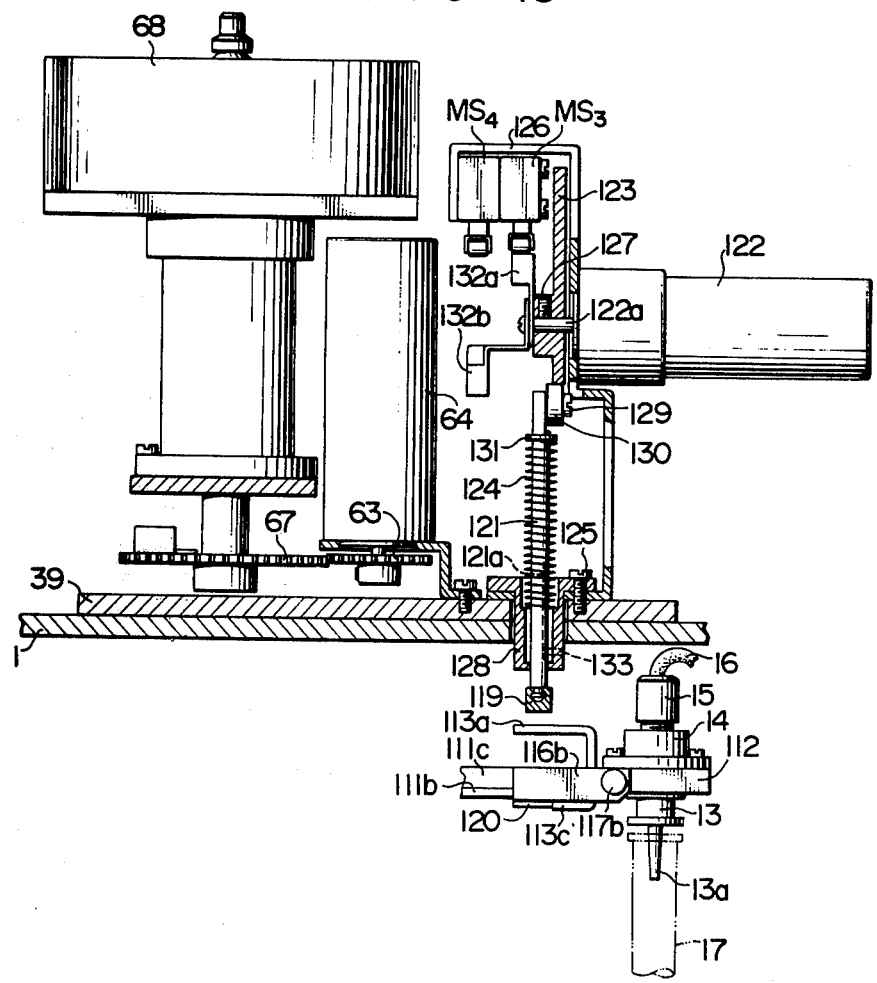
FIG. 13 is a side elevation, partly in section, taken along the line X—X shown in FIG. 11.

Referring to FIG. 13, the mechanism which tilts the cylinder 13 comprises an elevating shaft 121 engageable with the tilting driver 113. A motor 122 is mounted on an upstanding bracket 126 which is fixedly connected, by set screw 125, with the disc 39 which is in turn secured to the stationary plate 1. An eccentric cam 123 is fixedly mounted on the output shaft 122a of the motor by set screw 127. The elevating shaft 121 freely extends through a cylindrical guide and bearing member 128 which is secured to the disc 39 by the set screw 125 and which extends through the disc and the plate 1 to a position above the driver 113. The upper end of the shaft 121 is located adjacent to the cam 123, and fixedly carries a pin 129 on which a roller 130 is rotatably mounted for engagement with the cam 123. The pusher member 119 is secured to the lower end of the elevating shaft 121. Adjacent it its upper end, the shaft 121 fixedly carries an abutment ring 131, and a coiled compression spring 124 is disposed thereon to extend between the ring and the bearing member 128.

A pair of actuators 132a, 132b are mounted on the output shaft 122a for operating a pair of microswitches MS3, MS4, respectively, which are fixedly mounted on the bracket 126. These microswitches serve controlling the motor 120.

The bearing member 128 is threadably engaged by a radially extending pin 133, the free end of which extends into a longitudinal flute 121a formed in the shaft 121. As a result, a rotation of the shaft 121 is prevented while permitting an axial movement thereof.

Before describing the operation of the agitating apparatus, it is to be noted that the motor 122 is operated in timed relationship with the motor 27 which drives the fixed displacement pump 18 (see FIG. 1), in a manner to be described later which is determined by a control device, not shown. It is desirable that a culture vessel 2 containing a culturing solution be disposed on the peripheral surface of the turntable 3 which is inclined downwardly in a radially outward direction, as shown in FIG. 10.

In order to agitate a culturing solution 135 contained in the culture vessel 2, the pipette 17 is lowered to a phantom line position shown in FIG. 10 so that its lower end is sufficiently immersed in the solution 135 at a position offset to one side of the vessel. When the motor 122 is set in motion to rotate the eccentric cam 123 under this condition, the latter operates through the roller 130 to move the shaft 121 axially downward. Thereupon, the pusher member 119 secured to the lower end thereof pushes down the upper limb 113a of the driver 113, so that the support member 112 connected therewith rotates counter-clockwise about the axis defined by the screws 117a, 117b. The pipette 17 is then tilted through a given angle about the same axis. When the motor 122 is continuously rotated, the pipette 17 undergoes a periodic oscillating motion within the given angular extent. The oscillation of the pipette 17 within the culturing solution 135 achieves an agitation thereof.

In accordance with the invention, during the periodic oscillation of the pipette 17 in the culturing solution, the pump 18 is activated to cause it to withdraw and discharge the air within the tubing 16 alternately, thus alternating the withdrawal of the culturing solution 135 into the pipette 17 and the discharge of the solution from the pipette 17 into the vessel 2. The arrangement is such that the culturing solution is withdrawn when the pipette 17 assumes a vertical position while the solution is discharged when the pipette 17 assumes a tilted position. In the example shown, since the vessel 2 is disposed on an inclined peripheral surface of the turntable 3, the pipette 17 extends deep into the culturing solution to withdraw a sufficient amount thereof and discharge it to a region where the depth of the solution is reduced, thus assuring that the discharged solution flow to the region where it was withdrawn. By the combined use of the tilting of the pipette 17 and the withdrawal and discharge operation of the culturing solution, there is achieved a satisfactory agitation effect which is sufficient to release the cells, attaching to the bottom of the vessel 2, completely therefrom and suspend them in the culturing solution. It will be noted that the cells in suspension are withdrawn by the pipette 17 and conveyed thereby to the turntable 5 where they are discharged into a centrifuge tube 4 in the manner mentioned above.

What is claimed is:

1. Apparatus for liquid disposal and distribution in an automatic culture system, comprising a first turntable carrying a plurality of culture vessels which are disposed thereon on a common circumference and at an equal spacing, a second turntable carrying a plurality of centrifuge tubes which are disposed thereon on a common circumference and at an equal spacing, a pipette holding arm having its one end disposed to be angularly movable in a horizontal plane between part of the circumference on which the culture vessels are disposed and part of the circumference on which the centrifuge tubes are disposed, the other end of the arm being supported by and driven by a rotary and elevating mechanism, a tapered, pipette fitting cylinder secured to said one end of the pipette holding arm and having an opening formed therein for suction and discharge, a fixed displacement pump connected through a tubing with the opening of the cylinder, and a pipette holder, a pipette remover and a liquid disposal pot disposed at corresponding positions on the path of angular movement of the cylinder which is secured to the arm, the pipette holding arm detachably carrying a pipette for distribution of liquid into the culture vessel and the centrifuge tube and for disposing unnecessary liquid from the culture vessel.

2. Apparatus according to claim 1 in which the rotary and elevating mechanism associated with the pipette holding arm comprises an elevating shaft to which said other end of the arm is secured, the elevating shaft being adapted to move in the vertical direction by a drive from a motor which is transmitted through a combination of a rotatively driven gear and its meshing rack, another gear driven by a second motor for driving the elevating shaft for rotation, and a pair of encoders controlling the operation of the motors so that the pipette can be moved between the culture vessel, centrifuge tube, pipette holder, pipette remover and liquid disposal pot through angular and vertical movement of the arm.

3. Apparatus according to claim 1 in which the pipette fitting cylinder includes a tapered projection which is adapted to be tightly fitted into a central opening formed in a plug secured to the top opening of the pipette, thus detachably holding the pipette.

4. Apparatus according to claim 1 in which the fixed displacement pump is of a syringe type and has a capacity which is less than the volume of the pipette.

5. Apparatus according to claim 4 in which the fixed displacement pump includes a piston rod which is driven by a reversible motor through a combination of a pinion and rack.

6. Apparatus according to claim 1 in which the pipette holder, pipette remover and liquid disposal pot are located at a pipette loading position, a pipette removal position and a liquid disposal position, respectively, located on the path along which the cylinder moves angularly during a rotation of the pipette holding arm through nearly one-half revolution.

7. Apparatus according to claim 6 in which the pipette loading position is located toward the second turntable while the liquid disposal position is located toward the first turntable, and wherein the pipette removal position is located intermediate the pipette loading and liquid disposal positions.

8. Apparatus according to claim 1 in which the pipette holder comprises a guide sleeve for permitting a free fall of a pipette therethrough toward a given position as it is fed one by one from a pipette feeder, a pipette loading plate disposed below the guide sleeve and having a distal end which is in vertical alignment with the guide sleeve and which is formed with a semi-circular notch, a movable piece having a notch formed therein which is complementary to that formed in the loading plate and connected with the loading plate, and a spring for urging the movable piece into abutment against the loading plate so that the notches formed in the respective members define a tapered circular slot in vertical alignment with the guide sleeve when the movable plate is abutting relationship with the loading plate, thereby receiving a pipette as it falls down through the guide sleeve.

9. Apparatus according to claim 1 in which the pipette remover comprises a removal arm capable of angularly moving in one direction from a home position, a stationary shaft for rotatably carrying one end of the removal arm, a spring extending between the stationary shaft and the removal arm for normally urging the other end of the latter onto the path of angular movement of the cylinder, and an opening formed in the other end of the removal arm, allowing the projection of the cylinder to extend therethrough, the tapered projection of the cylinder which is exposed above a pipette being engaged with the opening in the removal arm and then the cylinder driven upward to remove the pipette from the tapered projection.

10. Apparatus for agitating a culturing solution comprising a pipette for withdrawing and discharging a culturing solution from or into a culture vessel, a pipette fitting cylinder for holding the pipette by a fitting engagement therewith, a pipette holding arm including a free end which is capable of carrying the cylinder in a tiltable manner, means for periodically tilting the cylinder while a pipette carried by the cylinder is immersed in the culturing solution in the culture vessel, and means for withdrawing and discharging the culturing solution into or from the pipette in timed relationship with the tilting movement of the cylinder.

11. Apparatus according to claim 10 in which the pipette fitting cylinder is secured to a support member which is tiltably mounted on the free end of the pipette holding arm and normally maintained in upright position by a tilting driver which is secured to the support member.

12. Apparatus according to claim 10 in which said means for tilting the cylinder comprises an elevating shaft for driving the tilting driver, an eccentric cam driven for rotation by a motor for causing a downward movement of the elevating shaft, and a spring urging the shaft to move upward, the elevating shaft moving down to push the driver to cause the support member to be tilted, thus tilting the pipette through the cylinder.

13. Apparatus according to claim 10 in which said means for withdrawing and discharging the culturing solution comprise a fixed displacement pump connected with the cylinder for producing a liquid withdrawal and discharge operation.

14. Apparatus according to claim 10 in which the culture vessel is disposed in an inclined position so that the pipette is located deep into the culturing solution when the latter is withdrawn, the liquid being discharged from the pipette to a region of the vessel which is remote from the withdrawal position where the liquid depth is reduced.

* * * * *